United States Patent
Ouwerkerk et al.

(10) Patent No.: US 10,448,874 B2
(45) Date of Patent: Oct. 22, 2019

(54) VISIT DURATION CONTROL SYSTEM AND METHOD

(71) Applicant: KONINKLIJKE PHILIPS N.V., Eindhoven (NL)

(72) Inventors: Martin Ouwerkerk, Culemborg (NL); Marjolein Irene Van Lieshout, Waalre (NL); Johannes Weda, Nijmegen (NL); Vincent Alexander Rudolf Aarts, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 488 days.

(21) Appl. No.: 14/774,706

(22) PCT Filed: Feb. 13, 2014

(86) PCT No.: PCT/IB2014/058963
§ 371 (c)(1),
(2) Date: Sep. 11, 2015

(87) PCT Pub. No.: WO2014/140960
PCT Pub. Date: Sep. 18, 2014

(65) Prior Publication Data
US 2016/0029939 A1    Feb. 4, 2016

Related U.S. Application Data

(60) Provisional application No. 61/776,975, filed on Mar. 12, 2013.

(51) Int. Cl.
*A61B 5/16* (2006.01)
*A61B 5/053* (2006.01)
(Continued)

(52) U.S. Cl.
CPC .............. *A61B 5/165* (2013.01); *A61B 3/112* (2013.01); *A61B 5/021* (2013.01);
(Continued)

(58) Field of Classification Search
CPC ..... A61B 5/165; A61B 5/021; A61B 5/02405; A61B 5/0476; A61B 5/0531;
(Continued)

(56) References Cited

U.S. PATENT DOCUMENTS 7,991,462 B2    8/2011  Storm
2003/0236451 A1*  12/2003  El-Nokaly ............... A61B 5/16
                                              600/300
(Continued)

FOREIGN PATENT DOCUMENTS

WO    2009138923 A1    11/2009
WO    2011156272 A1    12/2011
(Continued)

OTHER PUBLICATIONS

'Cortisol and Children's Adjustment: The Moderating Role of Sympathetic Nervous System Activity' by El-Sheikh et al. published in Journal of Abnormal Child Psychology on May 2008 (vol. 36 Issue-4, p. 601-611).*

(Continued)

*Primary Examiner* — Gary Jackson
*Assistant Examiner* — Zahed Kabir

(57) ABSTRACT

A visit duration control system comprises a sensor (10) for sensing one or more physiological parameters of a person over time allowing the quantification of stress load of said person, a visit detector (20) for indicating the start of a third party's visit to said person, a processor (30) for determining said person's stress load from said one or more physiological parameters during said third party's visit and a signaling (Continued)

unit (40) for issuing a warning signal if said stress load exceeds a predetermined level.

13 Claims, 4 Drawing Sheets

(51) Int. Cl.
| | |
|---|---|
| A61B 5/021 | (2006.01) |
| A61B 5/024 | (2006.01) |
| A61B 5/0476 | (2006.01) |
| A61B 3/11 | (2006.01) |
| A61B 5/00 | (2006.01) |
| G06K 9/00 | (2006.01) |
| G16H 50/30 | (2018.01) |

(52) U.S. Cl.
CPC ........ *A61B 5/02405* (2013.01); *A61B 5/0476* (2013.01); *A61B 5/0531* (2013.01); *A61B 5/0533* (2013.01); *A61B 5/681* (2013.01); *A61B 5/7275* (2013.01); *A61B 5/746* (2013.01); *G06K 9/00885* (2013.01); *G16H 50/30* (2018.01); *A61B 5/02438* (2013.01); *A61B 5/7242* (2013.01); *A61B 5/7282* (2013.01); *A61B 5/7475* (2013.01); *G06K 2009/00939* (2013.01)

(58) Field of Classification Search
CPC ..... A61B 5/0533; A61B 5/7275; A61B 5/746; A61B 3/112; A61B 5/117; A61B 5/02438; A61B 5/7242; A61B 7282/7475; G06K 9/00885; G06K 2009/00939
USPC ........................................................ 600/301
See application file for complete search history.

(56) References Cited

U.S. PATENT DOCUMENTS

| | | | | |
|---|---|---|---|---|
| 2007/0150202 | A1* | 6/2007 | Wiegand | G01N 33/6863 702/19 |
| 2010/0113893 | A1* | 5/2010 | Cohen | A61B 5/0205 600/301 |
| 2011/0001605 | A1* | 1/2011 | Kiani | G06F 19/3418 340/5.6 |
| 2011/0245633 | A1* | 10/2011 | Goldberg | A61B 5/681 600/301 |
| 2011/0301433 | A1 | 12/2011 | Sadowsky et al. | |
| 2012/0208195 | A1* | 8/2012 | de Rijk | C12Q 1/6883 435/6.11 |
| 2012/0277603 | A1 | 11/2012 | Camenzind et al. | |
| 2013/0116578 | A1* | 5/2013 | An | A61B 5/0205 600/484 |
| 2013/0225950 | A1* | 8/2013 | Van Elswijk | A61B 5/165 600/309 |
| 2013/0232103 | A1* | 9/2013 | Saeed | G06N 5/003 706/46 |
| 2013/0338470 | A1 | 12/2013 | Ouwerkerk | |
| 2014/0031704 | A1* | 1/2014 | De Vries | A61B 5/0533 600/485 |
| 2014/0107504 | A1* | 4/2014 | Stapelfeldt | A61B 5/4821 600/485 |
| 2014/0112556 | A1* | 4/2014 | Kalinli-Akbacak | G10L 25/63 382/128 |
| 2014/0288401 | A1 | 9/2014 | Ouwerkerk et al. | |
| 2016/0112681 | A1* | 4/2016 | Kaestle | A61B 5/11 348/78 |
| 2016/0180694 | A1* | 6/2016 | Rosenberg | A61B 5/1176 704/274 |
| 2017/0000398 | A1* | 1/2017 | Ouwerkerk | A61B 5/7239 |

FOREIGN PATENT DOCUMENTS

| | | | |
|---|---|---|---|
| WO | 2012117304 A1 | 9/2012 | |
| WO | 2012140537 A1 | 10/2012 | |
| WO | 2012164534 A1 | 12/2012 | |
| WO | WO-2013076615 A1 * | 5/2013 | ........... A61B 5/0533 |

OTHER PUBLICATIONS

Bell, L.; Family Visitation in the Adult ICU; 2011; American Association of Critical Care Nurses; pp. 1-7.

Bellodi, L., et al.; Dialogue Support for Memory Impaired People; 2012; IEEE Signal & Information Processing Association Annual Summit and Conference; pp. 1-4.

Cullen, L., et al.; Family and Pet Visitation in the Critical Care Unit; 2003; Critical Care Nurse; 23(5)62-67.

Fumagalli, S., et al.; Reduced Cardiocirculatory Complications with Unrestrictive Visiting Policy in an Intensive Care Unit; 2006; Circulation; 113:946-952.

Gunther, A. C., et al.; Skin conductance variability in ICU patients: an observational study of the relation to pain and Motor Activity Assessment Scale level; 2011; Critical Care; 15 (Suppl 1)p. 356.

* cited by examiner

VISIT DURATION CONTROL SYSTEM AND METHOD

CROSS REFERENCE TO RELATED APPLICATIONS

This application is a national filing of PCT application Serial No. PCT/IB2014/058963, filed Feb. 13, 2014, published as WO 2014/140960 A1 on Sep. 18, 2014, which claims the benefit of U.S. provisional application Ser. No. 61/776,975 filed Mar. 12, 2013, which is incorporated herein by reference.

FIELD OF THE INVENTION

The present invention relates to a visit control duration system and method. Further, the present invention relates to a processing device and method and to a computer program for implementing said processing method.

BACKGROUND OF THE INVENTION

In the past decades the visiting policies of intensive care units (ICUs) have been liberated considerably. Cullen et al, Family and Pet Visitation in the Critical Care Unit, Critical Care Nurse 23 (2003) p. 62-67 advocated in 2003 that family and even pet visits of the ICU are very beneficial. In 2011 (L. Bell, Family Visitation in the Adult ICU, AACN Practice Alert November 2011) the American Association of Critical Care Nurses issued a practice alert in which unrestricted visitation is advocated. In a section on supporting evidence it is mentioned that some ICU nurses believe that family visitation increases physiologic stress in the patient, and is mentally exhausting to patients and families, but quote evidence that this is not true. As an example of the quoted references Fumagalli S, Boncinelli L, Lo Nostro A, et al., Reduced cardiocirculatory complications with unrestricted visiting policy in an intensive care unit: results from a pilot, randomized trial, Circulation, 2006, 113:946-952 can be mentioned. Therein, they only compare a situation of unrestricted versus restricted visitation. Then no differences are found.

SUMMARY OF THE INVENTION

It is an object of the present invention to provide a visit duration control system and method that optimally controls the duration of a visit of third parties to a person or the performing of an exercise by the person, in particular a patient or a young mother, to avoid a too high physiological stress of the person caused by a too long visit and/or a too long exercise.

In a first aspect of the present invention a visit duration control system is presented that comprises
 a sensor for sensing one or more physiological parameters of a person over time allowing the quantification of stress load of said person,
 a visit detector for indicating the start of a third party's visit to said person,
 a processor for determining said person's stress load from said one or more physiological parameters during said third party's visit and
 a signaling unit for issuing a warning signal if said stress load exceeds a predetermined level.

In a further aspect of the present invention a processing device is presented comprising a processor that is configured to
 determine a person's stress load from one or more received physiological parameters of a person over time during a third party's visit, said one or more physiological parameters of said person allowing the quantification of stress load of said person, and
 control a signaling unit to issue a warning signal if said stress load exceeds a predetermined level.

In yet further aspects of the present invention, there are provided corresponding methods, a computer program which comprises program code means for causing a computer to perform the steps of the processing method when said computer program is carried out on a computer as well as a non-transitory computer-readable recording medium that stores therein a computer program product, which, when executed by a processor, causes the processing method disclosed herein to be performed.

Preferred embodiments of the invention are defined in the dependent claims. It shall be understood that the claimed processing device, the methods, computer program and medium have similar and/or identical preferred embodiments as the claimed stress monitoring device and as defined in the dependent claims.

It has been found that the feeble condition of an ICU patient or the temporarily weak condition of a young mother or of any other patient suffering from a health issue can be endangered by a too long and too arousing visit by a third party, e.g. a friend, a family member, a doctor or a member of the hospital staff. The proposed visit duration control system and method offer a means to quantify the (emotional and/or physiological) stress brought about by the visit and a universally understood means to signal that the visit needs to be terminated for the benefit of the patient's or mother's health. In the prior art no attempt has been found to quantify arousal and stress of such visits by means of scientifically accepted methods, such as salivary cortisol or skin conductance measurements.

Generally, various options exist for the use of the sensor. According to a preferred embodiment said sensor comprises one or more of a heart rate sensor for sensing heart rate or heart rate variability of said person, a skin conductance sensor for sensing skin conductance of said person, an EEG sensor for sensing an EEG of said person, a pupil sensor for sensing pupil dilatation of said person and a blood pressure sensor for sensing blood pressure of said person.

The processor is preferably configured to determine a cumulative stress signal indicating the stress load of the person from the start of the third party's visit. Further, in said embodiment said processor is configured to determine if said cumulative stress signal exceeds a predetermined stress threshold and to control said signaling unit to issue said warning signal if said predetermined stress threshold is exceeded.

In these embodiments said sensor preferably comprises a skin conductance sensor for sensing skin conductance of said person over time and said processor is configured to determine said cumulative stress signal by summing the sensed skin conductance over time, in particular by summing the rising edges of the sensed skin conductance over time. Alternatively, said sensor comprises a heart rate sensor for sensing heart rate or heart rate variability of said person over time and wherein said processor is configured to determine said cumulative stress signal by summing the time during which the heart rate variability is within predetermined heart rate variability thresholds. Both alternatives can also be used in combination to further increase the accuracy and reliability of the visit duration control system.

According to another embodiment said sensor comprises a skin conductance sensor for sensing skin conductance of said person over time, wherein said processor is configured to determine an estimated cortisol level trace from the sensed skin conductance and to determine said person's stress load from said estimated cortisol level trace. This provides an effective and accurate way of determining the person's stress load.

The signaling unit can be embodied in many different ways and can be configured to issue an audible, visible and/or sensible warning signal. In an embodiment said signaling unit comprises a first signaling element for issuing a first warning signal if said stress load exceeds a first predetermined level, allowing the visitors some time to put an end to their visit, and a second signaling element for issuing a second warning signal if said stress load exceeds a second predetermined level that is higher than said first predetermined level or if a predetermined time duration has passed.

The visit detector can also be embodied in many different ways. In a simple embodiment the visit detector comprises a user interface for manually entering the start of a third party's visit to said person. Thus, for instance the person himself, the third party visiting the person or a person working in the surrounding of the person (e.g. a nurse) may simply press a button when the visit starts.

In a more advanced embodiment the visit detector comprises a detector for automatically detecting a third party visiting said person. Thus, based on this automatic recognition the start of a visit is detected and indicated. Preferably, said detector comprises a camera and an identification unit for discriminating said person, third parties visiting said person and/or persons working or being continuously present at the place where said person is located. For instance, based face recognition or recognition of clothing persons working in a hospital can be discriminated from a patient and from visitors of the patient. In another embodiment voice recognition may be used for this purpose.

Preferably, said visit detector is configured for indicating the end of a third party's visit to said person and said processor is configured to estimate a recovery time of said person after the end of a visit. Thus, for instance, another signal may be issued by the signaling unit if said recovery time has passed, and or the signaling unit may indicate if or if not the recovery time is over. The recovery time can e.g. be estimated by use of a prediction algorithm described in the yet unpublished international patent application PCT/IB 2012/056354 which is herein incorporated by reference.

The visit duration control system may have different forms and may be implemented by use of one or more physical entities. In a preferred embodiment it is integrated into a wearable device that is wearable or attachable to the person's body, in particular integrated into a wristband, belt, mobile phone, watch or jewelry. In another embodiment only the sensor is attached to the person, but the sensor signal is transmitted to another device, e.g. in contactless manner to a computer, which then performs the processing. The result is then transmitted, e.g. in a contactless manner as well, to the signaling unit which again may be a separate unit, e.g. arranged visually in the room where the person is located.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
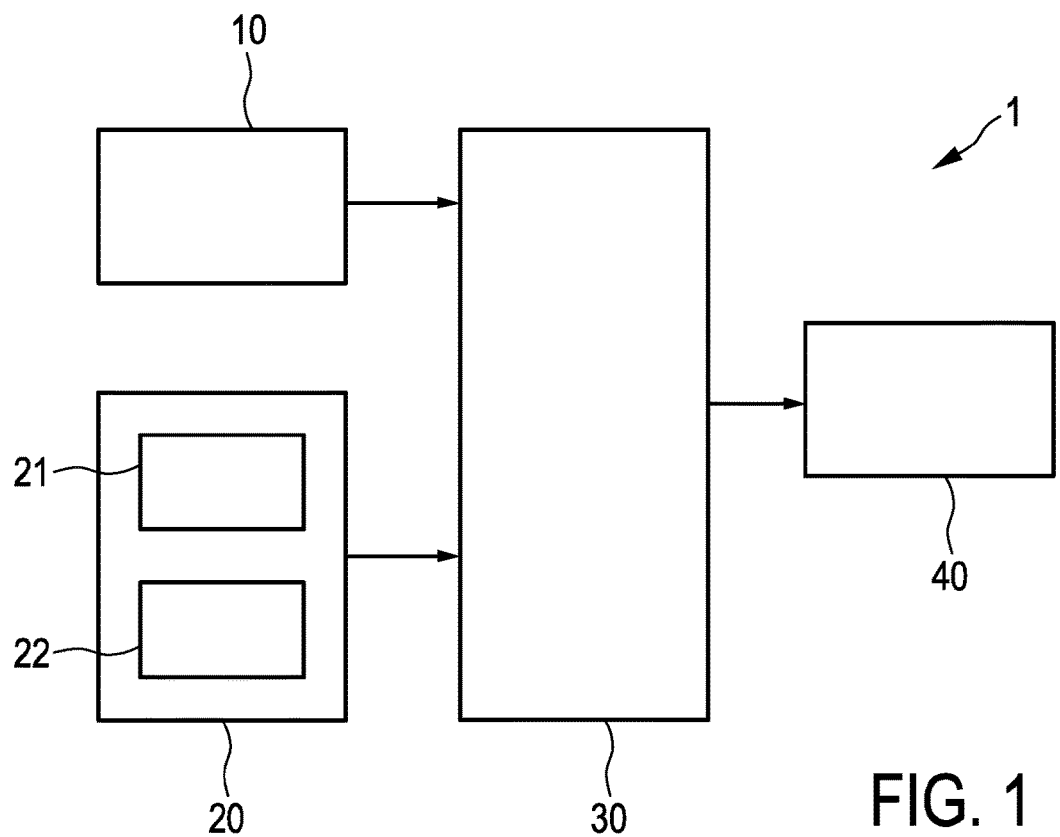
FIG. 1 shows a schematic diagram of a first embodiment of a visit duration control system according to the present invention.

FIG. 1 shows a schematic diagram of a first embodiment of a visit duration control system 1 according to the present invention. This embodiment is designed for use as a visit control system for controlling the duration of a visit to a person, e.g. a family visit of a patient in a hospital or a young mother. The visit duration control system 1 comprises a sensor 10 for sensing one or more physiological parameters of a person over time allowing the quantification of stress load of said person. The sensor 10 comprises or is implemented as e.g. a skin conductance sensor 11 for sensing skin conductance of said person over time. Said skin conductance sensor is attached to the person, e.g. as part of a watch, a separate wristband or body sensor worn in the kind of a belt.

Further, a visit detector 20 is provided for indicating the start of a third party's visit to said person. Said visit detector may include a camera 21 and a recognition unit 22 that recognizes visitors from image or video data recorded by the camera.

The sensed one or more physiological parameters, e.g. the sensed skin conductance over time, are provided to a processor 30 for determining said person's stress load from said one or more physiological parameters during said third party's visit. Said stress load is e.g. determined from a cumulative stress signal indicating the stress load of the person from the start of the third party's visit, said start being indicated by said visit detector 20. Said processor 30 can be implemented within the same device as the sensor 10 and the visit detector 20.

Finally, a signaling unit 40 is provided for issuing a warning signal if said stress load exceeds a predetermined level. Said signaling unit 40 may have different forms, e.g. may issue a visible warning signal like a traffic light, an audible warning signal like a special tone and/or a sensible warning signal like a vibration.

The feeble condition of a patient such as, but not limited to, an ICU patient can be endangered by a too long and too arousing family or doctor visit. During investigations in a hospital several visits were observed where hospital staff had to ask the visitors to leave in the interest of the patient. Some cases will be presented as an example. It is to be understood that, although the following examples describe visits by family members, the invention can equally be applied to measure the stress level of a patient or young mother during visits by doctors and members of the hospital staff, for example to discuss the patient's status or the patient's management, for example when discussing the possible patient's discharge.

Figure 2A:
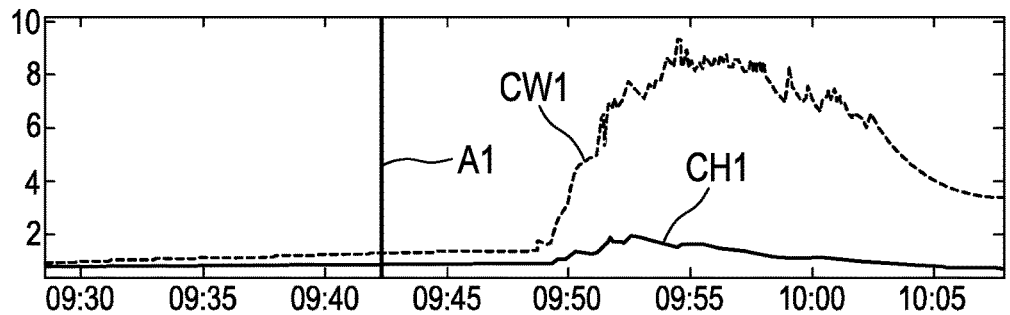
FIG. 2 shows exemplary diagrams of skin conductance and heart rate trace of a first patient.
Figure 2B:
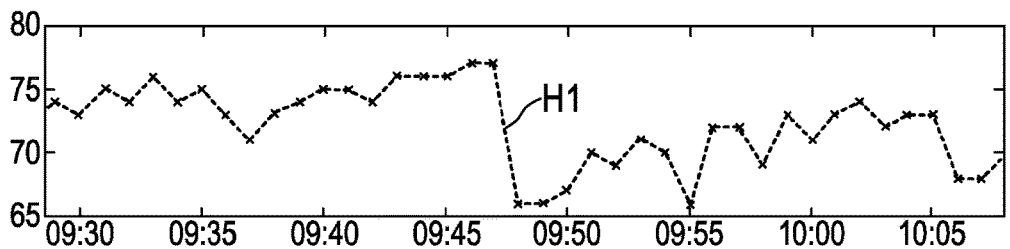

In a first scenario next to the regular monitoring of a first patient, such as heart rate, the skin conductance was measured of this patient during a visit of family in the ICU. FIG. 2A shows skin conductance CH1 measured at the traditional palmar position and the skin conductance CW1 measured at the volar side of the wrist. FIG. 2B shows the averaged heart frequency H1 as obtained from the hospital's clinical information system for ICUs.

The following observations were made during a family visit to the patient. The visitors arrived at 9:42 hrs (indicated by the line A1 in FIG. 2A). The patient was asleep. At 9:49 hrs the patient woke up. The family started talking and touching the patient. At 9:56 hrs the nurse was hoping the family will leave soon. At 9:59 hrs the nurse talked to patient and family. They agreed to leave. At 10:00:24 hrs the family left.

In agreement with the above explained observations of Fumagalli et al. the heart rate (HR) drops as a result of the visit. The skin conductance, however, shows considerable arousal of the patient. After the visit the skin conductance trace slowly returns to the original level, without further peaks. This example shows that when the nurse is alert, and safeguards the condition of the patient, only a limited impact of the visit takes place, and the patient's health is not endangered.

Figure 3A:
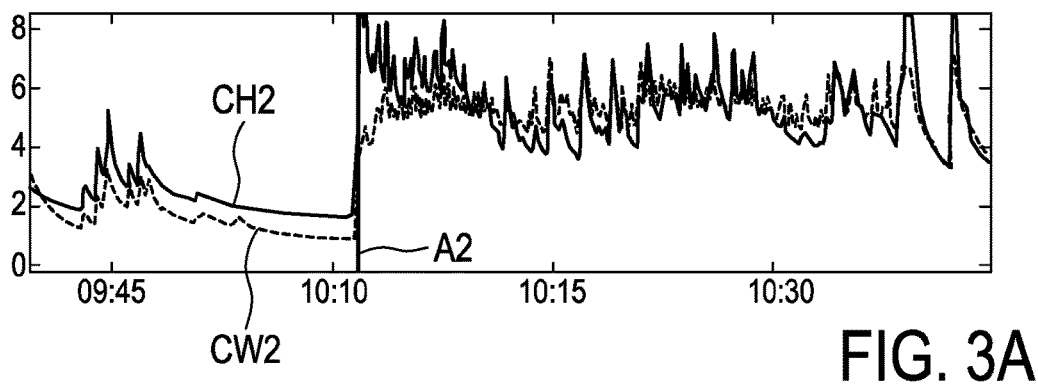
FIG. 3 shows exemplary diagrams of skin conductance and heart rate trace of a second patient.
Figure 3B:
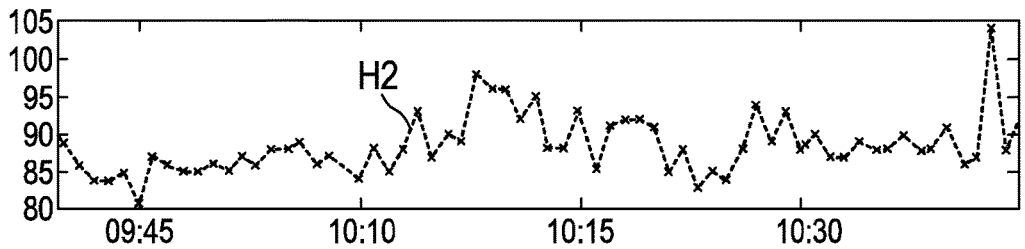

In a second scenario similar information is obtained as in the first scenario. FIG. 3A shows skin conductance CH2 measured at the traditional palmar position and the skin conductance CW2 measured at the volar side of the wrist. FIG. 3B shows the averaged heart frequency H2 as obtained from the hospital's clinical information system for ICUs.

At 9:45 hrs the patient was informed about the upcoming detubation. At 9:55 hrs the patient was lying quietly in bed. At 10:02 hrs husband and son of the patient arrived. They held the patient's hand and stroke over the arm. At 10:24 hrs the observation was that the patient lied quietly. It should be noticed that the skin conductance signals CW2 and CH2 suggests strong arousal. At 10:26 hrs the nurse talked to the family about the patient. At 10:38 hrs the husband kissed the patient and at 10:39:28 hrs the family left.

The heart frequency of this patient rises somewhat during the visit. During the 35 minute visit the arousal level of the patient has been high, with lots of emotional stimuli. This patient was less aroused by the message of detubation than by the visit. A long period of excitement can certainly burden a patient, and possibly harm recovery.

The conventional patient monitoring equipment did signal some effect brought about by the visits, but the skin conductance measured at the wrist or at the palmar side of the hand was able to signal the patient's arousal in a clear-cut way. This offers a means to quantify the emotional stress brought about by the family visit that can be linked to a skin conductance system is the processor, which quantifies the cumulative arousal. For instance the cumulative rising edges of the skin conductance trace can serve as a measure in a preferred embodiment. When a preset quantity is exceeded a signal can be given to patient, staff and/or visitors that the visit needs to be terminated for in the interest of the patient. A simple traffic light like signaling unit is an example of a universally understood means to signal that the visit needs to be terminated for the benefit of the patient's health.

A second target group of this invention is young (preferably first time) mothers in the first weeks after they delivered a baby. These mothers are usually very proud, very happy, very frequently visited, but still recovering from the delivery, under the influence of postnatal hormone rushes and potentially very tired from sleep deprivation. Furthermore, these mothers know that they are not patients and that they can perfectly well deal with very busy and demanding lives, which they were leading when they were not mothers yet. They are also used to fully recover from busy days by enjoying very long nights of undisturbed sleep. The risk that is present among these mothers is that they overestimate themselves, their physical condition and their stamina. A close observer that takes good care of the young mother potentially is someone who takes care that visits do not take too long and that the mother gets enough rest. However, when such an observer is not present or is too overwhelmed him/herself, a more objective stress limiter can be used to guard the mother's emotional stress limits and by that her recovery process and general sanity.

Generally, such a visit duration control system can not only be applied to patients or young mothers, but to any persons performing a stressful task (which may also be the job of said person).

Figure 4:
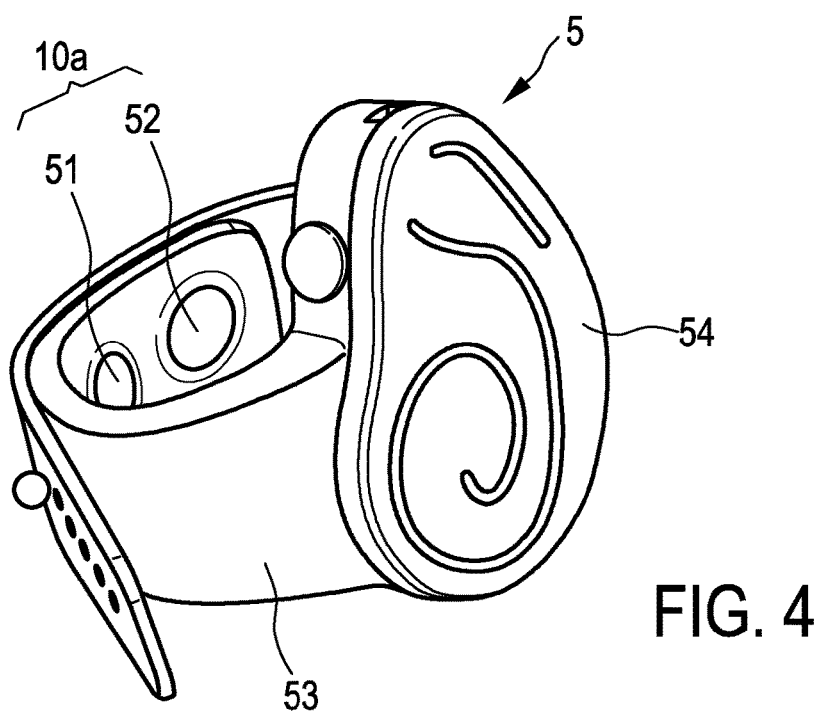
FIG. 4 shows a practical implementation of a visit duration control system according to the present invention in the form of a wristband.

The stress of a person is preferably measured by means of a skin conductance sensor. As an example skin conductance wristband is an unobtrusive wearable device that is particularly suited for the purpose. Such a wearable device is e.g. described in WO 2012/140537 A1; a dry skin conductance electrode that can be used here for measuring skin conductance is described in WO 2012/117304 A1. The content of these publications is herein incorporated by reference. A perspective view of an embodiment of such a wearable device 2 in the form of a wristband wearable by a person (e.g. a patient) is depicted in FIG. 4.

The wristband comprises a wristband material part 53 and a casing 54. The wristband material part 53 can loop around the wrist of the user. It will be understood that the wearable device 5 could also be worn around any other suitable body part, such as the ankle, foot or hand.

The wearable device 5 can in particular comprise some or all of the elements of the patient monitoring system 1 described herein. For instance, in an embodiment a complete patient monitoring system 1 can be provided in an unobtrusive and wearable format can be provided. Alternatively, the wearable device 5 can only comprise the sensor 10 and the other elements of the patient monitoring system 1 are located at a remote location or device (e.g. a remote computer).

At least, the wearable device 5 comprises the sensor, in this embodiment a skin conductance sensor 10a. The skin conductance sensor 10a comprises skin conductance electrodes 51, 52 in combination with a skin conductance measuring unit (not shown). In the embodiment of FIG. 9, two skin conductance electrodes 51, 52 are integrated into the wrist band material part 53. The skin conductance electrodes 51, 52 can be arranged so as to contact the volar side of the wrist, where there is normally not a lot of hair, when the wearable device 5 is put on or worn by the user. In this way, a better measurement of the skin conductance can be provided.

The skin conductance measuring unit is adapted to measure the skin conductance of the user between the skin conductance electrodes 51, 52. The skin conductance electrodes 51, 52 can be connected to the skin conductance measuring unit by means of wires integrated in the wristband material part 53 in the embodiment of FIG. 4. In particular, the skin conductance measuring unit or sensor can comprise a voltage generator for applying a voltage between the at least two skin conductance electrodes, a sensing unit for sensing a current between the at least two electrodes, and/or a calculating unit for calculating the skin conductance based on the sensed current. The measured skin conductance over time forms the skin conductance trace (or data). The skin conductance trace (or data) can for example be stored in a memory of the wearable device 5, or can be (e.g. wirelessly) transmitted to an external unit using a (wireless) transmitter.

The skin conductance measuring unit and/or the processor 20 can be integrated into the casing 54 of the wearable device 5. The wearable device 5 can further comprise a transmitter for wirelessly transmitting data over a wireless communication link, such as the output data or the estimated stress level. However, it will be understood that the processor 20 can also be a separate part or device and that the wearable device 5 then transmits the skin conductance data to the separate part or device via the (wireless) transmitter.

Further, the visit detector 30 can be integrated into the wearable device 5, e.g. in the form of a button or touchscreen so that the user can enter the start (and, preferably, the end) of a visit. Alternatively, the visit detector can be a separate part or device (e.g. an interface arranged at the door or a nurse, a door sensor sensing if someone enters or leaves the room and/or a presence detector for sensing the presence of persons in the room). The wearable device 5 may then receive the information about the start of a visit by a (preferably wireless) receiver from said external visit detector. Alternatively, this indication is also transmitted from the external visit detector to the external processor for further processing.

Still further, the signaling unit 40 can be integrated into the wearable device 5, e.g. in the form of an optical signaling element (e.g. a blinking LED or other signal on a screen), an audible sound emitter emitting an audible warning signal and/or a haptic feedback unit such as vibrator starting to vibrate representing the warning signal). The signaling unit can also be configured to issue a silent signal that the cumulative stress is too high. Alternatively, the signaling unit 40 can be a separate part or device (e.g. an optical and/or audible signaling unit arranged at a wall or a signaling unit arranged at a remote location, e.g. the room of the nurse) to which the processor is able to transmit information. Further, in an embodiment the person's, visitor's and/or caregiver's mobile phone or other electronic device can be used to output the warning signal.

In a practical implementation the wearable device 5 comprises a built-in microcontroller which can process the raw skin conductance data and to obtain a measure for the cumulative stress caused by a visit. Further, a built-in Bluetooth transceiver is included that allows sending instructions to a signaling unit that signals visitors that it is time to leave. It can instead of sending instructions stream the raw skin conductance data to a computer, where data processing takes place. Based on the results of the data processing the computer can control the signaling unit.

The wearable device can also have different forms. For instance, it can have the form of a body belt worn by the user or it can be portable and can be clipped to a belt of the user.

The sensor 10 of the visit duration control system 1 can further comprise other sensor elements, such as an electrocardiogram (ECG) sensor, like an ECG chest belt. The ECG sensor can sense the electrocardiogram of the user. From the electrocardiogram the heart rate variability (HRV) can be determined, which is known to relate to stress. However, also other suitable measurements such as biologically variable perfusion (BVP), respiration, skin temperature, electroencephalography (EEG)/brain activity, activity measurement (e.g. through an accelerometer) and/or questionnaires can be used for alternative and/or additional measurements. Thus, the sensor 10 may comprise one or more of a heart rate sensor for sensing heart rate or heart rate variability of said person over time, a skin conductance sensor for sensing skin conductance of said person, an EEG sensor for sensing an EEG of said person, a pupil sensor for sensing pupil dilatation of said person and a blood pressure sensor for sensing blood pressure of said person.

In case of using the visit duration control system as visit duration control system the arrival and presence of visitors needs to be known to the system. Hospital staff frequently visits the patient during the day. Thus, preferably a means to discriminate visitors from hospital staff is provided. A simple means is to request visitors to press a button upon arrival. A more reliable method is to use a camera 21 and a recognition unit 22, as shown in FIG. 1, for instance to use an available video monitoring system of the ICU. The obtained images or video data can then be analyzed, for instance for non-hospital clothing or for an identifier identifying a visitor and/or a staff member of the hospital. In another embodiment facial recognition of family members and staff may be used allowing the discrimination between staff members and visitors. Still further, in an embodiment the hospital staff may signal the arrival of visitors to the visit duration control system.

Figure 5:
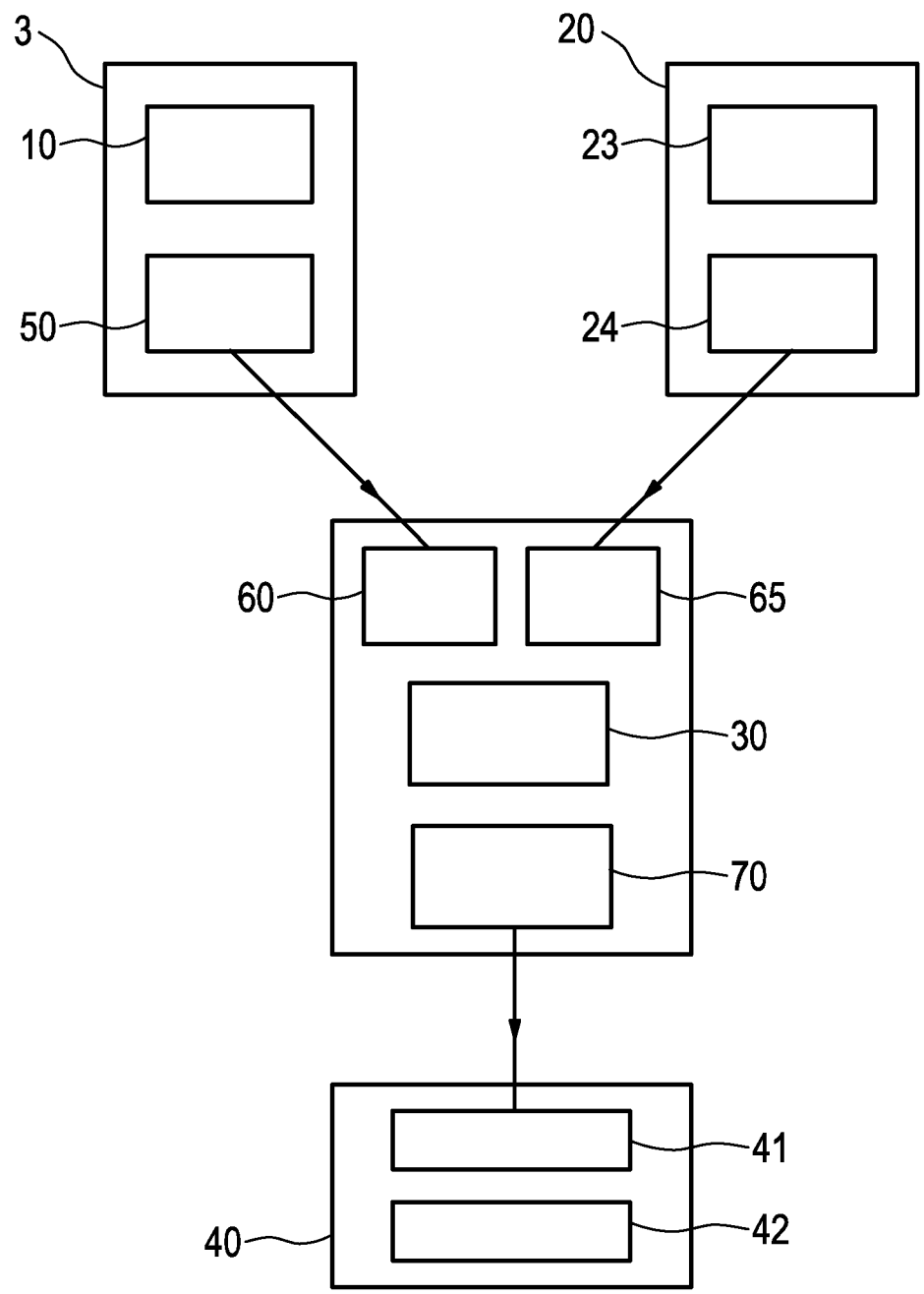
FIG. 5 shows a schematic diagram of a second embodiment of a visit duration control system according to the present invention.

Another embodiment of a visit duration control system 2 according to the present invention is schematically depicted in FIG. 5. In this embodiment the sensor 10 is integrated into a wearable device 3, such as the user's watch or a separate wristband as shown in FIG. 4. The wearable device 3 further comprises a transmitter (e.g. a Bluetooth or WLAN transmitter) for transmitting the measured signal (e.g. a skin conductance signal) to a processor 30.

The processor 30 is arranged at a remote location and is e.g. part of a computer, workstation or hospital data processing system 4 that further comprises a corresponding receiver 60 (e.g. a Bluetooth or WLAN receiver) for receiving the measured signal from the sensor 10.

The visit detector 20 is again arranged as a separate entity, for instance at a different location, e.g. at an entrance control where a person enters (and later deletes) a visitor visiting the user into the system 2 by use of a user interface 23 (such as a computer running a visitor registration software or a simple button). Alternatively, the visit detector 20 comprises a camera 21 and a recognition unit 22 as shown in FIG. 1. Further, the visit detector 20 comprises a transmitter (e.g. a Bluetooth or WLAN transmitter, or a wired connection, such as a LAN connection) for transmitting the visit detector signal to the processor 30 which comprises a corresponding receiver 65 (which may be different or identical to the receiver 60).

The signaling unit 40 is also arranged as a separate entity, for instance in the room where the user is located. The processor comprises a transmitter 70 (e.g. a wired or wireless transmitter) for transmitting a control signal to the signaling 40 to issue a warning signal at the right moment. The signaling unit comprises a corresponding receiver 41 and a signaling element 42, such as a display and/or loudspeaker.

The cumulative stress can be computed in various ways. A preferred method uses a wearable stress load predictor with coping coaching. In particular, in an embodiment a (salivary) cortisol level trace (which is a cortisol level over time) is estimated or modeled based on skin conductance measurements. It is known that a stimulus (or stressor or emotional event) causes (with a short latency) a stimulus response in the skin conductance (or skin conductance response) which can be measured. There is a specific relationship between a stimulus response (or skin conductance response) in the skin conductance trace and a (salivary) cortisol time response of a user. Thus, there is a specific correlation between the measured skin conductance response (or stimulus response) and a subsequent cortisol response. The cortisol response linked to a stimulus response has in particular a specific (time) latency. This latency is in particular much bigger than the latency between the stimulus and its stimulus response. In particular, it has been found that there is a specific latency between the peak in the skin conductance trace and the peak of the corresponding cortisol time response. Further, the cortisol time responses can be cumulated or added on top of each other.

Using this knowledge, the level of stress of a user can be estimated. In particular, a quantification of the cumulative effect of subsequent stimuli (or stressors) in a specific time frame (e.g. a time frame of several hours) can be provided. Thus, not only the allostatic load can be assessed, but even a prediction of an altered stress response in the near future can be given after the occurrence of severe stimuli (or stressors). Allostatic load is similar to cumulative stimulus response severity (or balance/imbalance state), but the time lag is absent. Thus, by use of this method a measure for the person's stress load can be derived from skin conductance measurements. Further details can be found in yet unpublished international patent application PCT/IB 2012/056354 which is herein incorporated by reference.

Another method to determine cumulative stress is to determine the height of the rising edges in micro Siemens of the arousal peaks in the skin conduction signal, and summate these values. When a preset limit is reached, the signal is given that the visit needs to be terminated to prevent excessive stress.

Figure 6A:
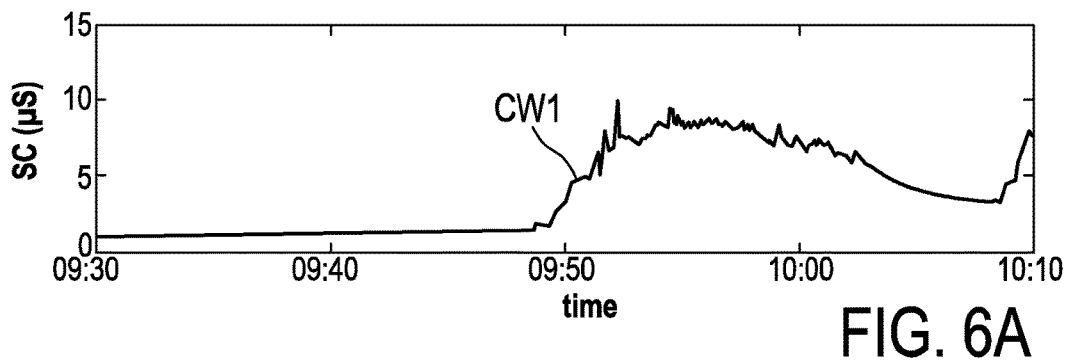
FIG. 6 shows exemplary diagrams of skin conductance and the cumulative sum of rising edges of said skin conductance of said first patient.
Figure 6B:
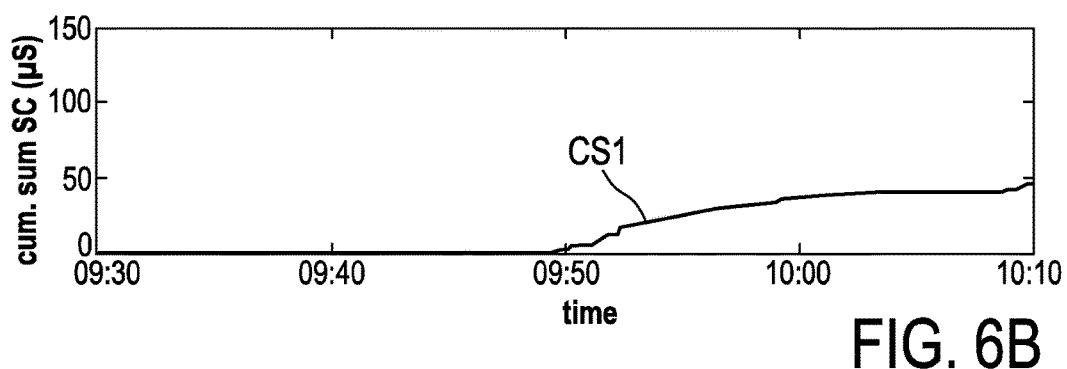

FIGS. 6 and 7 illustrate how cumulative stress can be estimated for the cases of the above mentioned examples illustrated with reference to FIGS. 2 and 3. FIG. 6A shows substantially the same skin conductance trace CW1 as shown in FIG. 2A. FIG. 6B shows the cumulative sum CS1 of rising edges of the skin conductance trace CW1. It can be seen from the cumulative sum signal CS21 that from the moment the patient woke up (at 9:49 hrs) when the family is present, the cumulative sum of rising edges quickly starts increasing and only ceases to increase when the family has left just after 10:00 hrs.

Figure 7A:
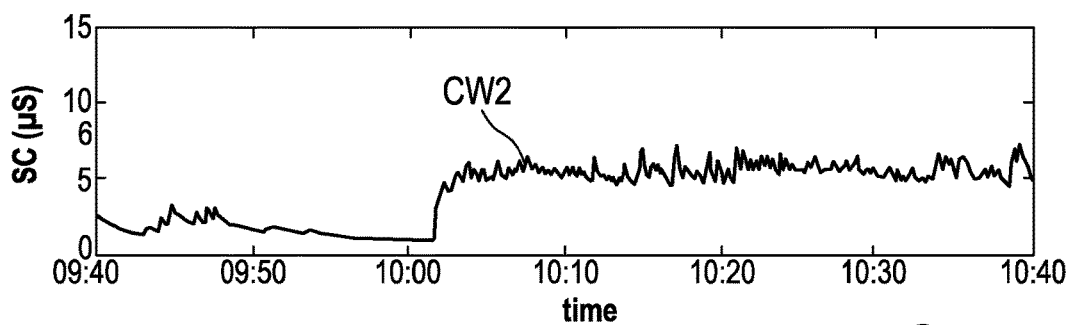
FIG. 7 shows exemplary diagrams of skin conductance and the cumulative sum of rising edges of said skin conductance of said second patient.
Figure 7B:
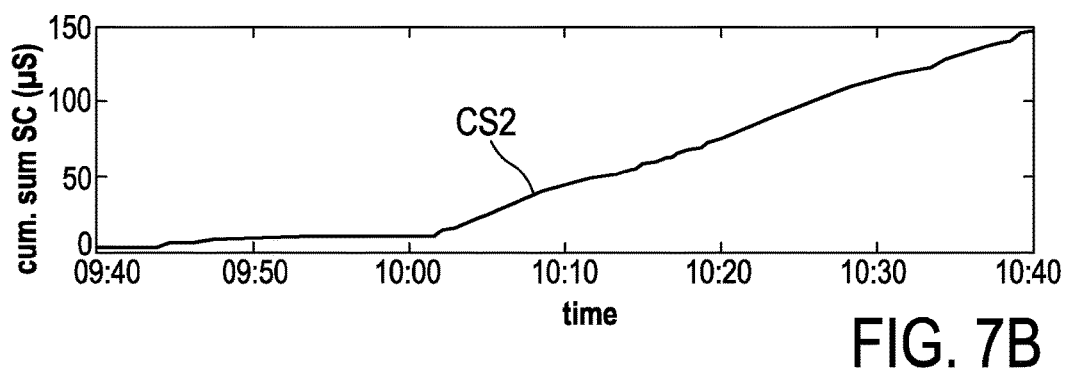

FIG. 7A shows substantially the same skin conductance trace CW2 as shown in FIG. 3A. FIG. 7B the cumulative sum CS2 of rising edges of the skin conductance trace CW2. This cumulative sum signal CS2 shows an almost continuous rise of the cumulative sum of rising edges, starting from the moment the family arrived (at 10:02 hrs) and continuing throughout their stay.

In a preferred embodiment the processor 30 monitors and evaluates the cumulative sum of the rising edges by watching its value and, preferably, the speed with which it is increasing. Based thereon the cumulative stress the monitored person has undergone is estimated. Based on this estimation, an advice can be given to the visitors, caregivers and/or monitored person to discontinue a visit to the person.

As a simple signaling unit a traffic light like unit is proposed in an embodiment. The size needs to be adjusted to fit the location where it is to be used. The green light is on when the condition of the person (e.g. patient/young mother) is not endangered. The yellow light switches on when a first predetermined percentage, e.g. 90 percent, of the maximum allowable stress load/arousal has been measured. For instance when the cumulative rising edge of the skin conductance signal has risen to 45 micro Siemens the yellow light switches on. This signals the visitors to leave. The red light switches on when a second predetermined percentage, e.g. 100 percent, of the maximum allowable stress load/arousal has been measured, i.e. at 50 micro Siemens cumulative rising edge. Alternatively or additionally an audio signal may accompany the yellow and red visual signals. For the person whose measured signals are shown in FIGS. 2 and 6 this level is not reached, whereas for the person whose measured signals are shown in FIGS. 3 and 6 the cumulative rising edge continues to rise way beyond it.

In the above mentioned wearable stress load predictor with coping coaching the duration is given how long the physical effect of the undergone stress lasts. For women it is about 120 minutes and for men 150 minutes. These durations can be taken into account in a prediction of a recovery time, upon which the patient has a clean slate, and the calculation of the stress load effect of visitors starts at zero again.

Further, in an embodiment said processor is configured to remember which persons cause the highest stress load in previous visits, and warn them to be more quiet this visit, or warn staff to be on alert for stress related complications.

Still further, in an embodiment the sensor comprises a heart rate sensor for sensing heart rate or heart rate variability of said person over time. In this case the processor determines said cumulative stress signal by summing the time during which the heart rate variability is within predetermined heart rate variability thresholds.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A visit duration control system comprising:
   a device wearable by a person, the device comprising:
   a band to be wrapped around an appendage of the person;
   a casing coupled to the band, wherein the casing comprises a skin conductance sensor for sensing a skin conductance of the person, the skin conductance sensor coupled to the casing;
   a visit detector for indicating the start of a third party's visit to said person, wherein said visit detector comprises a detector for automatically detecting a third party visiting said person and wherein said detector comprises a camera and an identification unit for discriminating among said person, third parties visiting said person and/or persons working or being continuously present at the place where said person is located;
a processor, wherein the processor is configured to:
receive sensor input comprising skin conductance before the third party's visit and during the third party's visit;
determine one or more skin conductance traces based on the sensor input regarding skin conductance of the person received over the duration of the third party's visit;
determine a plurality of stimulated responses in the one or more skin conductance traces;
determine a plurality of estimated cortisol-level traces of the person based on the plurality of stimulated responses, wherein each respective estimated cortisol-level trace of the plurality of estimated cortisol-level traces extends an amount of time after a respective stimulated response of the plurality of stimulated responses; and
calculate with said sensor input both a baseline stress load of the person and a second stress load of the person during said third party's visit based on the plurality of cortisol-level traces; and
a signaling unit for issuing a warning signal if the difference between the second stress load and the baseline stress load of the person exceeds a predetermined level.

2. The visit duration control system as claimed in claim 1, wherein said processor is configured to determine a cumulative stress signal indicating the stress load difference of the person from the start of the third party's visit.

3. The visit duration control system as claimed in claim 2, wherein said processor is configured to determine if said cumulative stress signal exceeds a predetermined stress threshold and to control said signaling unit to issue said warning signal indicating that the visit needs to be terminated for the benefit of the patient's health if said predetermined stress threshold is exceeded.

4. The visit duration control system as claimed in claim 2, wherein said sensor comprises a skin conductance sensor for sensing skin conductance of said person over time and wherein said processor is configured to determine said cumulative stress signal by summing the sensed skin conductance over time, in particular by summing the height of rising edges of the sensed skin conductance over time.

5. The visit duration control system as claimed in claim 2, further comprising a heart rate sensor for sensing heart rate or heart rate variability of said person over time and wherein said processor is configured to determine said cumulative stress signal by summing the time during which the heart rate variability is within predetermined heart rate variability thresholds.

6. The visit duration control system as claimed in claim 1, wherein said sensor comprises a skin conductance sensor for sensing skin conductance of said person over time and wherein said processor is configured to determine an estimated cortisol level trace from the sensed skin conductance and to determine said person's baseline stress load and second stress load from said estimated cortisol level trace.

7. The visit duration control system as claimed in claim 1, wherein said signaling unit comprises a first signaling element for issuing a first warning signal indicating that the visit needs to be terminated for the benefit of the patient's health if said difference between the second stress load and the baseline stress load exceeds a first predetermined level and a second signaling element for issuing a second warning signal indicating that the visit needs to be terminated for the benefit of the patient's health if said difference between the second stress load and the baseline stress load exceeds a second predetermined level that is higher than said first predetermined level or if a predetermined time duration has passed.

8. The visit duration control system as claimed in claim 1, wherein said visit detector comprises a user interface for manually entering the start of a third party's visit to said person.

9. The visit duration control system as claimed in claim 1, wherein said visit detector is configured for indicating the end of the third party's visit to said person and wherein said processor is configured to estimate a recovery time of said person after the end of the visit.

10. The visit duration control system as claimed in claim 1, wherein said visit duration control system is integrated into the wearable device that is wearable or attachable to the person's body, in particular integrated into a wristband, belt, mobile phone, watch or jewelry.

11. A processing device comprising a processor that is configured to:
determine baseline stress load of a person based on cortisol-level traces of the person before a third party's visit, said cortisol-level traces of said person allowing the quantification of stress load of said person;
automatically detect a third party visiting said person;
discriminate among said person, third parties visiting said person and/or persons working or being continuously present at the place where said person is located;
determine a person's visitation stress load from the cortisol-level traces of said person over time during said third party's visit, said cortisol-level traces of said person allowing quantification of stress load of said person; and
control a signaling unit to issue a warning signal indicating that the visit needs to be terminated for the benefit of the patient's health if the difference between the baseline stress load and the visitation stress load exceeds a predetermined level, wherein quantifying the stress load based on the plurality of cortisol-level traces of the person comprises:
determining one or more skin conductance traces based on input from a sensor regarding skin conductance of the person received over the duration of the third party's visit;
determining a plurality of stimulated responses in the one or more skin conductance traces; and
determining a plurality of estimated cortisol-level traces of the person based on the plurality of stimulated responses, wherein each respective estimated cortisol-level trace of the plurality of estimated cortisol-level traces extends an amount of time after a respective stimulated response of the plurality of stimulated responses.

12. A processing method comprising
determining baseline stress load of a person based on cortisol-level traces of the person before a third party's visit, said cortisol-level traces of said person allowing the quantification of stress load of said person;
automatically detecting a third party visiting said person;
discriminating among said person, third parties visiting said person and/or persons working or being continuously present at the place where said person is located;

determining a person's visitation stress load from the cortisol-level traces of said person over time during said third party's visit, said cortisol-level traces of said person allowing quantification of stress load of said person; and controlling a signaling unit to issue a warning signal indicating that the visit needs to be terminated for the benefit of the patient's health if the difference between the baseline stress load and the visitation stress load exceeds a predetermined level, wherein quantifying the stress load based on the plurality of cortisol-level traces of the person comprises:

determining one or more skin conductance traces based on input from a sensor regarding skin conductance of the person received over the duration of the third party's visit;

determining a plurality of stimulated responses in the one or more skin conductance traces; and determining a plurality of estimated cortisol-level traces of the person based on the plurality of stimulated responses, wherein each respective estimated cortisol-level trace of the plurality of estimated cortisol-level traces extends an amount of time after a respective stimulated response of the plurality of stimulated responses.

13. A computer program for use in conjunction with a computer processor, wherein the computer program is operable when used with the computer processor to:

determine a baseline stress load of a person based on cortisol-level traces of the person before a third party's visit, said cortisol-level traces of said person allowing the quantification of stress load of said person;

automatically detect a third party visiting said person;

discriminate among said person, third parties visiting said person and/or persons working or being continuously present at the place where said person is located;

determine a person's visitation stress load from the cortisol-level traces of said person over time during said third party's visit, said cortisol-level traces of said person allowing quantification of stress load of said person; and control a signaling unit to issue a warning signal indicating that the visit needs to be terminated for the benefit of the patient's health if the difference between the baseline stress load and the visitation stress load exceeds a predetermined level, wherein quantifying the stress load based on the plurality of cortisol-level traces of the person comprises:

determining one or more skin conductance traces based on input from a sensor regarding skin conductance of the person received over the duration of the third party's visit;

determining a plurality of stimulated responses in the one or more skin conductance traces; and determining a plurality of estimated cortisol-level traces of the person based on the plurality of stimulated responses, wherein each respective estimated cortisol-level trace of the plurality of estimated cortisol-level traces extends an amount of time after a respective stimulated response of the plurality of stimulated responses.

* * * * *